(12) United States Patent
Dawson et al.

(10) Patent No.: US 6,569,443 B1
(45) Date of Patent: May 27, 2003

(54) TOPICAL TREATMENT OR PREVENTION OF OCULAR INFECTIONS

(75) Inventors: Chandler R. Dawson, Mill Valley, CA (US); Lyle M. Bowman, Pleasanton, CA (US)

(73) Assignee: Insite Vision, Inc., Alameda, CA (US)

( * ) Notice: Subject to any disclaimer, the term of this patent is extended or adjusted under 35 U.S.C. 154(b) by 0 days.

(21) Appl. No.: 09/767,943

(22) Filed: Jan. 24, 2001

Related U.S. Application Data

(63) Continuation of application No. 09/346,923, filed on Jul. 2, 1999, now Pat. No. 6,239,113, which is a continuation-in-part of application No. 09/282,165, filed on Mar. 31, 1999, now abandoned.

(51) Int. Cl.⁷ .......................... A61F 2/00; A61F 13/00; A61K 31/70
(52) U.S. Cl. .......................... 424/433; 424/427; 514/29
(58) Field of Search ........................... 514/29; 424/427, 424/433

(56) References Cited

U.S. PATENT DOCUMENTS

| | | |
|---|---|---|
| 4,474,768 A | 10/1984 | Bright |
| 4,512,982 A | 4/1985 | Hauske et al. |
| 4,517,359 A | 5/1985 | Kobrehel et al. |
| 4,551,456 A | 11/1985 | Katz |
| 4,692,454 A | 9/1987 | Mich et al. |
| 4,851,415 A | 7/1989 | Mich et al. |
| 5,188,826 A | 2/1993 | Chandrasekaran et al. |
| 5,192,535 A | 3/1993 | Davis et al. |
| 5,250,518 A | 10/1993 | Kobrehel et al. |
| 5,340,572 A | 8/1994 | Patel et al. |
| 5,441,939 A | 8/1995 | Yang |
| 5,498,699 A | 3/1996 | Djokic et al. |
| 5,605,889 A | 2/1997 | Curatolo et al. |
| 5,631,004 A | 5/1997 | Cagle et al. |
| 5,767,153 A | 6/1998 | Bowman et al. |
| 5,814,655 A | 9/1998 | Patel et al. |
| 5,872,104 A | 2/1999 | Vermeulen et al. |
| 5,977,171 A | 11/1999 | Bowman et al. |
| 6,159,458 A | 12/2000 | Bowman et al. |
| 6,239,113 B1 | 5/2001 | Dawson et al. |
| 6,265,444 B1 | 7/2001 | Bowman et al. |
| 6,309,630 B1 | 10/2001 | Patel et al. |

FOREIGN PATENT DOCUMENTS

| | | |
|---|---|---|
| EP | 0 126 684 B1 | 11/1984 |
| EP | 0 142 426 | 5/1985 |
| EP | 0 298 650 | 1/1989 |
| EP | 0 391 909 | 10/1990 |
| EP | 0 445 743 A2 | 9/1991 |
| EP | 0 445 743 B1 | 9/1991 |
| EP | 0 467 331 B1 | 1/1992 |
| EP | 0 677 530 B1 | 10/1995 |
| EP | 0 679 400 B1 | 11/1995 |
| EP | 0 879 823 A1 | 11/1998 |
| EP | 0925 789 A1 | 6/1999 |
| EP | 0 925 789 | 6/1999 |
| EP | 1075837 A2 | 2/2001 |
| JP | (Kokai) 11-240838 | 9/1999 |
| WO | WO 95/09601 | 4/1995 |
| WO | 96 19489 | 6/1996 |
| WO | 96 20010 A | 7/1996 |
| WO | WO 98/17280 | 4/1998 |

OTHER PUBLICATIONS

Programme for the Prevention of Blindness and Deafness Alliance for the Global Elimination of Trachoma, "Planning for the Global Elimination of Trachoma (GET) Report of the WHO Consultation", Geneva, Switzerland (Nov. 25 & 26, 1996).

Programme for the Prevention of Blindness and Deafness Alliance for the Global Elimination of Trachoma, "Report of the First Meeting of the WHO Alliance for the Global Elimination of Trachoma", Geneva, Switzerland (Jun. 30–Jul. 1, 1997).

Programme for the Prevention of Blindness and Deafness, "Report of the Second Meeting of the WHO Alliance for the Global Elimination of Trachoma", Geneva, Switzerland (Jan. 12–14, 1998).

Prevention of Blindness and Deafness Geneva, Switzerland, "Report of the Third Meeting of the WHO Alliance for the Global Elimination of Trachoma", Quarzazate, Morocco (Oct. 19–20, 1998).

Jururatanasirikul, S., et al., Distribution of azithromycin into brain tissue, cerebrospinal fluid, and aqueous humor of the eye. Antimicrobial Agents Chemotheraphy, 40:825–826 (1996).

Thylefors, B. Azithromycin: A new opportunity for control of trachoma. WHO Drug Information 10(3):132–133 (1996).

Bailey et al., Lancet vol. 3$^{rd.}$ pp. 453–456 (1993).

First Meeting of the WHO Alliance for the Global Elimination of Trachoma, Geneva, Jun. 30–Jul. 1, 1997.

Robert E. Leonard, II, Carol L. Karp, and Eduardo C. Alfonso, *Erythromycin, Clarithromycin, and Azithromycin*, 1997, Textbook of Ocular Pharmacology, pp. 515–523.

Robert H. Cross, Gary N. Holland, Samuel J. Elias and Rachel Tuz, *Corneal Pharmacokinetics of Topical Clarithromycin*, Apr. 1995, Investigative Opthalmology & Visual Science, vol. 36, No. 5, pp 965–968.

(List continued on next page.)

*Primary Examiner*—Elli Peselev
(74) *Attorney, Agent, or Firm*—Sughrue Mion, PLLC

(57) ABSTRACT

The topical application of an azalide antibiotic such as azithromycin to the eye is useful in treating or preventing ocular infections. In one embodiment, the azalide antibiotic is supplied to the eye in a depot for sustained release. A more convenient dosing regimen can also be provided by the use of an appropriate depot. Furthermore, a composition containing a combination of medicaments is also provided.

45 Claims, No Drawings

OTHER PUBLICATIONS

International Search Report PCT/US 00/07924, European Patent Office Mar. 14, 2001.

A comparison of oral azithromycin with topical oxytetracycline/polymyxin for the treatment of trachoma in children. Abstract XP–002161953, Biosis Information Service, Philadelphia, PA, 1997.

Oral vs. topical erythromycin therapies for chlamydial conjunctivitis. Abstract XP–002161954, Biosis Information Service, Philadelphia, PA, 1982.

Corneal pharmacokinetics of topical clarithromycin. Abstract XP–002161955, Biosis Information Service, Philadelphia, PA, 1995.

TOPICAL TREATMENT OR PREVENTION OF OCULAR INFECTIONS

This application is a continuation of application Ser. No. 09/346,923, filed Jul. 2, 1999 now U.S. Pat. No. 6,239,113, which is a continuation-in-part of prior U.S. patent application Ser. No. 09/282,165, filed Mar. 31, 1999, now abandoned each of which is herein incorporated by reference in its entirety.

BACKGROUND OF THE INVENTION

1. Field of the Invention

The present invention relates to a method for treating or preventing infections in the eye and to compositions useful therein.

2. Description of the Related Arts

The eye is susceptible to bacterial and parasitic infections arising from both traumatic and non-traumatic related events. Infections are a concern after ocular surgery and precautions are correspondingly taken to prevent the onset of infection. However, even without the invasive trauma of a surgical procedure, infections in the eyelids, conjunctiva, cornea, and other ocular tissues can arise.

Treating infections in ocular tissues can be challenging and/or problematic because of the difficulty in delivering an antibiotic to the affected tissue. In general, ocular infections are treated by local injection, systemic administration, or topical application of an antibiotic. The route of administration depends on the antibiotic selected, the location of the infection and the type of infection.

The simple and direct approach of topically applying the antibiotic to the exterior of the eye has several benefits, including the avoidance of side effects and the reduced chance of developing resistant strains of bacteria as compared to systemic administration. However, for a variety of reasons, many antibiotics are not amenable or suitable for topical application to the eye.

For example, in order for a topical application to be effective, the antibiotic must be able to penetrate the desired tissue. This may include penetrating the conjunctiva and the cornea. Also, the penetration rate must be sufficient to impart an effective dose. Many drugs do not possess a requisite penetration ability with regard to the tissues of the eye. It should be noted that the external layers of the eye are quite different from the tissues encountered in the stomach and intestinal tract. Thus, while a certain drug may be readily absorbed in the intestines and introduced into the blood supply for systemic administration, the same drug may be incapable of being absorbed by or passing through the substantially avascular outer layers of the conjunctiva or cornea at a minimally acceptable therapeutic concentration. The mechanism of transport or uptake of the drug is entirely different for topical administration than for oral administration.

Another concern is that the antibiotic will be toxic to the eye. A toxic response includes redness, swelling and/or discharge. Toxicity is especially problematic for topical administration because it is a concentration dependent phenomenon. The concentration ratio between tear fluid and ocular tissue in topical administration is generally in the range of about 1:500 to 1:1000, due to the penetration gradient. Thus, while a drug may be non-toxic at the minimum effective concentration, the 500% to 1000% increase in concentration associated with topical administration may well induce a toxic response. Again, the fact that oral or systemic administration shows the drug to be compatible with ocular tissue does not predict or address the toxicity issue associated with topical administration.

A further potential unsuitability of an antibiotic is the practicality of topical administration by the patient. Assuming that sufficiently high concentrations of the antibiotic can be used to achieve an effective dose within the target tissue without a toxic response, the application may nonetheless be irritating. An irritation response includes temporary burning, stinging and/or watering of the eye. Beyond whether the increased watering of the eyes washes away so much of the antibiotic composition that an effective dose is prevented, the patient may simply be resistant to complying with the dosage regimen because of the irritation. By failing to comply with the dosing regimen, the treatment efficacy is reduced or eliminated.

Some antibiotics have been found to sufficiently meet the above requirements so as to be applicable to topical administration. Examples of antibiotics that are reported to be useful in ocular topical administration include tobramycin, gentamycin, fluoroquinolone derivatives including norfloxacin, ofloxacin, and ciprofloxacin, naphthyridine, tetracyclines, and erythromycin. However, the dosing of the known topical antibiotics is usually an extensive and inconvenient regimen. Applying drops every 2 hours for the first two days and every 4 hours for the next several days is a common dosing regimen for aqueous solutions to treat ocular infections. But, such an extensive dosing regimen is inconvenient and obtaining patient compliance can be difficult. Of course, the greater the non-compliance with the regimen, the less effective the treatment.

It would be beneficial to find additional antibiotics that are capable of topical application in treating the eye. It would be further desirable to provide a topical formulation that is effective against a broad spectrum of bacteria and that can be administered in a less extensive regimen.

SUMMARY OF THE INVENTION

The present invention relates to a process for treating an eye that comprises topically applying an azalide antibiotic to an eye in an amount effective to treat or prevent infection in a tissue of the eye. Applicants have discovered that azalide antibiotics are suitable for topical administration to the eye. A preferred azalide antibiotic is azithromycin.

A preferred form of the invention involves forming or supplying a depot of the azalide antibiotic in contact with the eye for a sufficient length of time to allow a minimum inhibitory concentration (MIC) of the azalide antibiotic to diffuse into the cells of the targeted eye tissue(s). Once the MIC threshold has been surpassed, a therapeutically effective concentration of the azalide antibiotic will remain in the tissue(s) for a considerable period of time due to its long half-life. Accordingly, an advantage of certain preferred forms of the present invention is a simplified dosing regimen. For example, one or two topical applications may provide a sufficient tissue concentration that an inhibitory concentration remains resident in the infected tissue for several days, i.e. 4–12 days. Thus, a complete treatment regimen may involve only one or two topical applications.

The invention also relates to a topical ophthalmic composition containing an azalide antibiotic. In one embodiment, the ophthalmic composition is a sustained release composition comprised of an aqueous suspension of the azalide antibiotic and a polymer suspending agent.

DETAILED DESCRIPTION OF THE INVENTION

Azalides are a known subclass of macrolide antibiotics. Occasionally, the literature has also referred to these compounds as azolides, and the two spellings should be taken as having the same meaning. For the present invention and as used in this specification, an "azalide antibiotic" means a derivitized erythromycin A structure having a nitrogen atom inserted into the lactone ring. Additional variations from the erythromycin structure are also embraced within the term "azalide antibiotic." Such additional variations include the conversion of a hydroxyl group to an alkoxy group, especially methoxy (so-called "O-methylated" forms), for example at the 6 and/or 12 position. Such compounds are described in U.S. Pat. No. 5,250,518, the entire contents of which are incorporated herein by reference. Other variations relate to derivatives of the sugar moieties, for example, 3" desmethoxy derivatives and the formation of oxo or oxime groups on the sugar ring such as at the 4" position as described in U.S. Pat. No. 5,441,939, the entire contents of which are incorporated herein by reference. This patent also teaches that the adjacent hydroxyl groups at the 11 and 12 position of the lactone ring can be replaced with a single carbonate or thiocarbonate group. In short, an azalide antibiotic for purposes of the present invention is any derivative of the erythromycin structure that contains a 15-member lactone ring having a ring nitrogen, preferably at the 9 position, and a sugar group attached via a glycosidic bond to the lactone ring at the 5 position and at the 3 position, and which still exhibits bacteriostatic or bactericidal activity.

Preferred azalide antibiotics are represented by formula (I) and pharmaceutically acceptable salts thereof.

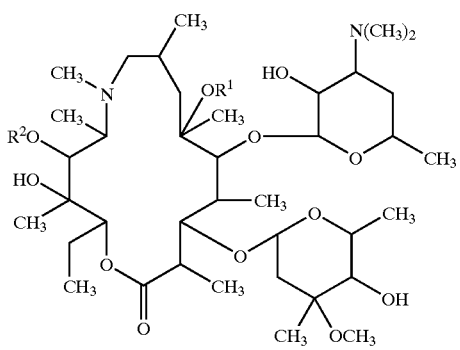

(I)

$R^1$ and $R^2$ each independently represent a hydrogen atom or a methyl group. Preferably at least one of $R^1$ and $R^2$ is a hydrogen atom. Azithromycin, the common name for N-methyl-11-aza-10-deoxo-10-dihydroerythromycin, corresponds to the compound of formula (I) where both $R^1$ and $R^2$ are a hydrogen atom. Azithromycin was disclosed in U.S. Pat. Nos. 4,474,768 and 4,517,359, the entire contents of each patent being incorporated herein by reference, and is the most preferred azalide antibiotic. In particular, the dihydride form of azithromycin is especially contemplated for use in the present invention, although other forms are also suitable.

Azithromycin has been used as an oral antibiotic and is sold worldwide under the brand name Zithromax® by Pfizer Inc. Azithromycin is a broad spectrum antibiotic that is generally more effective in vitro than erythromycin. Moreover, because azithromycin is an azalide and thus has a ring nitrogen atom, it exhibits improved acid-stability, half-life, and cellular uptake in comparison to erythromycin. The high uptake and retention of azithromycin into cells, including phagocytic blood cells, allows the systemically administered azithromycin to be nonetheless preferentially delivered to the site of the infection. The mechanism is believed to be as follows. The ingested azithromycin is absorbed through the intestine into the blood stream from which it enters most cells of the body including, inter alia, the white blood cells. In response to an infection within the body, white blood cells, including those containing azithromycin, are attracted to the infectious site. When the white blood cells die, the azithromycin is released. As more and more white blood cells arrive at the infectious site and die, the concentration of azithromycin in the surrounding tissue increases, eventually surpassing the MIC. Once at the infectious site, the azithromycin remains in the tissue for a prolonged period of time, due to its long half-life, such that an effective concentration of azithromycin is present at the infected site for many days after cessation of administration.

Although azithromycin can reach many of the tissues and fluids of the eye by oral administration, it has now been discovered that azalide antibiotics in general and azithromycin in particular are amenable to topical administration on the eye. The azalide antibiotic can be supplied to the eye surface in a variety of ways, including as an aqueous ophthalmic solution or suspension, as an ophthalmic ointment, and as an ocular insert, but application is not limited thereto. Any technique and ocular dosage form that supplies an azalide antibiotic to the external eye surface is included within the notion of "topically applying." Although the external surface of the eye is typically the outer layer of the conjunctiva, it is possible that the sclera, cornea or other ocular tissue could be exposed such as by rotation of the eye or by surgical procedure and thus be an external surface.

The amount of azalide antibiotic topically supplied is effective to treat or prevent infection in a tissue of the eye. This means that the conditions of application result in a retarding or suppression of the infection. Typically at least about $MIC_{50}$ for the targeted bacteria or parasite is delivered to the ocular tissue by the topical application of an effective amount. More concretely, the concentration within the ocular tissue is desired to be at least about 0.25 µg/g, preferably at least 1 µg/g, and more preferably at least 10 µg/g. The amount of azalide actually supplied to the external eye surface will almost always be much higher than the tissue concentration. This reflects the penetration hold up of the azalide antibiotic by the outer tissue layers of the eye and that penetration is to some extent concentration driven. Thus, supplying greater amounts to the exterior will drive more antibiotic into the tissues.

Where a series of applications are used in the dosing regimen, it is possible that one or more of the earlier applications will not achieve an effective concentration in the ocular tissue, but that a later application in the regimen will achieve an effective concentration. This is contemplated as being within the scope of topically applying an azalide antibiotic in an effective amount. However, generally a single application, such as consisting of one or two drops, provides a therapeutically effective concentration (e.g. one that retards or suppresses the infection) of the azalide antibiotic within a tissue of the eye. Indeed, although dependent on the amount and form of the ophthalmic composition, a single application will typically provide a therapeutically effective amount of the azalide antibiotic within a tissue of the eye for at least 8, preferably 12, and more preferably at least 18 hours.

The topical application of an azalide antibiotic can be used to treat or prevent a variety of conditions associated with ocular infection. For example, conditions of the lids including blepharitis, blepharconjunctivies, meibomianitis, acute or chronic hordeolum, chalazion, dacryocystitis, dacryoadenities, and acne rosacea; conditions of the conjunctiva including conjunctivitis, ophthalmia neonatorum, and trachoma; conditions of the cornea including co meal ulcers, superficial and interstitial keratitis, keratoconjunctivitis, foreign bodies, and post operative infections; and conditions of the anterior chamber and uvea including endophthalmitis, infectious uveitis, and post operative infections, are a few of the tissues and conditions that can be treated by topical application of an azalide antibiotic. The prevention of infection includes pre-operative treatment prior to surgery as well as other suspected infectious conditions or contact. Examples of prophylaxis situations include treatment prior to surgical procedures such as blepharoplasty, removal of chalazia, tarsorrhapy, procedures for the canualiculi and lacrimal drainage system and other operative procedures involving the lids and lacrimal apparatus; conjunctival surgery including removal of ptyregia, pingueculae and tumors, conjunctival transplantation, traumatic lesions such as cuts, burns and abrasions, and conjunctival flaps; corneal surgery including removal of foreign bodies, keratotomy, and comeal transplants; refractive surgery including photorefractive procedures; glaucoma surgery including filtering blebs; paracentesis of the anterior chamber; iridectomy; cataract surgery; retinal surgery; and procedures involving the extra-ocular muscles. The prevention of ophthalmia neonatorum is also included.

More generally, the azalide antibiotics can be used to treat or prevent ocular infections caused by a variety of bacteria or parasites, including but not limited to one or more of the following organisms: Staphylococcus including *Staphylococcus aureus* and *Staphylococcus epidermidis*; Streptococcus including *Streptococcus pneumoniae* and *Streptococcus pyogenes* as well as Streptococci of Groups C, F, and G and Viridans group of Streptococci; *Haemophilus influenza* including biotype III (*H. Aegyptius*); *Haemophilus ducreyi; Moraxella catarrhalis*; Neisseria including *Neisseria gonorrhoeae* and *Neisseria meningitidis*; Chlamydia including *Chlamydia trachomatis, Chlamydia psittaci*, and *Chlamydia pneumoniae*; Mycobacterium including *Mycobacterium tuberculosis* and *Mycobacterium avium*-intracellular complex as well as atypical mycobacterium including *M. marinum, M. fortuitm*, and *M. chelonae; Bordetella pertussis; Campylobacterjejuni; Legionella pneumophila; Bacteroides bivius; Clostridium perfringens; Peptostreptococcus species; Borrelia burgdorferi; Mycoplasma pneumoniae; Treponema pallidum; Ureaplasma urealyticum*; toxoplasma; malaria; and nosema.

The azalide antibiotic is applied to the exterior surface of the eye, usually in an ophthalmically acceptable composition which comprises an ophthalmically acceptable carrier and the azalide antibiotic. The "ophthalmically acceptable carrier" is used in a broad sense and includes any material or composition that can contain and release the azalide antibiotic and that is compatible with the eye. Typically the ophthalmically acceptable carrier is water or an aqueous solution or suspension, but also includes oils such as those used to make ointments and polymer matrices such as used in ocular inserts. Generally, azalide antibiotics are poorly soluble in water. However, water solubility is improved if converted to a salt form. For example, azithromycin dihydrochloride has good water solubility. Accordingly, an aqueous solution of an azalide antibiotic can be formed and used for topical application. But, more typically, an aqueous suspension is formed of the poorly soluble or insoluble azalide antibiotic. Ointments and solid dosage forms can also be used as delivery compositions as are well known in the art. The concentration of azalide antibiotic present in the ophthalmic composition depends upon the dosage form, the release rate, the dosing regimen, and the location and type of infection. Generally speaking, the concentration is from about 0.01 to 2%, more typically 0.1 to 1%, for fluid compositions and 0.5 to 50% for solid dosage forms, however, the compositions are not limited thereto.

The fluid ophthalmic compositions of the present invention, including both ointments and suspensions, have a viscosity that is suited for the selected route of administration. A viscosity in the range of from about 1,000 to 30,000 centipoise is useful for a drop. About 30,000 to about 100,000 centipoise is an advantageous viscosity range for ophthalmic administration in ribbon form. The viscosity can be controlled in many ways known to the worker skilled in the art.

The ophthalmic compositions may contain one or more of the following: surfactants, adjuvants including additional medicaments, buffers, antioxidants, tonicity adjusters, preservatives, thickeners or viscosity modifiers, and the like. Additives in the formulation may desirably include sodium chloride, EDTA (disodium edetate), and/or BAK (benzalkonium chloride), sorbic acid, methyl paraben, propyl paraben, chlorhexidine, and sodium perborate.

A further aspect of the present invention involves the above-mentioned use of additional medicaments in combination with the azalide antibiotic. A composition comprising an azalide antibiotic, an additional medicament, and an ophthalmically acceptable carrier can advantageously simplify administration and allow for treating or preventing multiple conditions or symptoms simultaneously. The "additional medicaments," which can be present in any of the ophthalmic compositional forms described herein including fluid and solid forms, are pharmaceutically active compounds having efficacy in ocular application and which are compatible with an azalide antibiotic and with the eye. Typically, the additional medicaments include other antibiotics, antivirals, antifungals, anesthetics, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; comolyn; lodoxamide; levocabastin; naphazoling; antazoline; and pheniramimane. These other medicaments are generally present in a pharmaceutically effective amount as is understood by workers of ordinary skill in the art. These amounts are generally within the range of from about 0.01 to 5%, more typically 0.1 to 2%, for fluid compositions and from 0.5 to 50% for solid dosage forms.

The aqueous ophthalmic compositions (solutions or suspensions) for use in the present invention use water which has no physiologically or ophthalmically harmful constituents. Typically purified or deionized water is used. The pH is adjusted by adding any physiologically and ophthalmically acceptable pH adjusting acids, bases or buffers to within the range of about 5.0 to 8.5. Examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, THAM (trishydroxymethylamino-methane), and the like. Salts and buffers include citrate/dextrose, sodium bicarbonate, ammonium chloride and mixtures of the aforementioned acids and bases.

The osmotic pressure ($\pi$) of the aqueous ophthalmic composition is generally from about 10 milliosmolar (mOsM) to about 400 mOsM, more preferably from 260 to 340 mOsM. If necessary, the osmotic pressure can beadjusted by using appropriate amounts of physiologically and ophthalmically acceptable salts or excipients. Sodium chloride is preferred to approximate physiologic fluid, and amounts of sodium chloride ranging from about 0.01% to about 1% by weight, and preferably from about 0.05% to about 0.45% by weight, based on the total weight of the composition, are typically used. Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can also be used in addition to or instead of sodium chloride to achieve osmolalities within the above-stated range. Similarly, a sugar such as mannitol, dextrose, sorbitol, glucose and the like can also be used to adjust osmolality.

A preferred form of the present invention provides achieving a sufficiently high tissue concentration with a minimum of doses so that a simple dosing regimen can be used to treat or prevent bacterial or parasitic infections. To this end, a preferred technique involves forming or supplying a depot of azalide antibiotic in contact with the external surface of the eye. A depot refers to a source of azalide antibiotic that is not rapidly removed by tears or other eye clearance mechanisms. This allows for continued, sustained high concentrations of azalide antibiotic to be present in the fluid on the external surface of the eye by a single application. In general, it is believed that absorption and penetration are dependent on both the dissolved drug concentration and the contact duration of the external tissue with the drug-containing fluid. As the drug is removed by clearance of the ocular fluid and/or absorption into the eye tissue, more drug is provided, e.g. dissolved, into the replenished ocular fluid from the depot.

Accordingly, the use of a depot more easily facilitates loading of the ocular tissue in view of the typically slow and low penetration rate of the generally water-insoluble/poorly soluble azalide antibiotics. The depot can effectively slowly "pump" the azalide antibiotic into the ocular tissue. As the azalide antibiotic penetrates the ocular tissue it is accumulated therein and not readily removed due to its long half-life. As more azalide antibiotic is "pumped" in, the tissue concentration increases and the minimum inhibitory concentration threshold is eventually reached and/or exceeded, thereby loading the ocular tissue with azalide antibiotic. By significantly exceeding the $MIC_{50}$, more preferably the $MIC_{90}$ level, provided the toxicity limit is not exceeded, a therapeutically effective concentration will remain active in the tissue for an extended period of time due to the low clearance rate of the azalide antibiotic from the tissue. Thus, depending on the depot, one or two applications may provide a complete dosing regimen. Indeed, such a simple dosing regimen may provide a 6 to 14 day treatment concentration within the ocular tissue. A preferred dosing regimen involves one to two doses per day over a one to three day period, more preferably one or two doses in a single day, to provide in vivo at least a 6 day treatment and more typically a 6 to 14 day treatment.

A depot can take a variety of forms so long as the azalide antibiotic can be provided in sufficient concentration levels therein and is releasable therefrom and that the depot is not readily removed from the eye. A depot generally remains for at least about 30 minutes after administration, preferably at least 2 hours and more preferably at least 4 hours. The term "remains" means that neither the depot composition nor the azalide antibiotic is exhausted or cleared from the surface of the eye prior to the indicated time. In some embodiments, the depot can remain for up to eight hours or more. Typical ophthalmic depot forms include aqueous polymeric suspensions, ointments, and solid inserts. Polymeric suspensions are the most preferred form for the present invention and will be discussed subsequently.

Ointments are well known ophthalmic compositions and are essentially an oil-based delivery vehicle. Typical ointments use a petroleum and/or lanolin base to which is added the active ingredient, usually as 0.1 to 2%, and excipients. Common bases include mineral oil, petrolatum and combinations thereof, but oil bases are not limited thereto. Since azalide antibiotics are frequently only sparingly soluble in water, an ointment is a logical form of administration. An ointment is usually applied as a ribbon onto the lower eyelid. The disadvantage of ointments is that they are difficult to administer, are messy, and uncomfortable/inconvenient to the patient; i.e. temporarily blurred vision is common.

Inserts are another well known ophthalmic dosage form and are comprised of a matrix containing the active ingredient. The matrix is typically a polymer and the active ingredient is generally dispersed therein or bonded to the polymer matrix. The active ingredient is slowly released from the matrix through dissolution or hydrolysis of the covalent bond, etc. In some embodiments, the polymer is bioerodible (soluble) and the dissolution rate thereof can control the release rate of the active ingredient dispersed therein. In another form, the polymer matrix is a biodegradable polymer that breaks down such as by hydrolysis to thereby release the active ingredient bonded thereto or dispersed therein. The matrix and active ingredient can be surrounded with a polymeric coating such as in the sandwich structure of matrix/matrix+active/matrix, to further control release as is well known in the art. The kinds of polymers suitable for use as a matrix are well known in the art. The azalide antibiotic can be dispersed into the matrix material or dispersed amongst the monomer composition used to make the matrix material prior to polymerization. The amount of azalide antibiotic is generally from about 0.1 to 50%, more typically about 2 to 20%. The insert can be placed, deperiding on the location and the mechanism used to hold the insert in position, by either the patient or the doctor and is generally located under the upper eyelid. A variety of shapes and anchoring configurations, if any, are well known in the art. Preferably a biodegradable or bio-erodible polymer matrix is used so that the spent insert does not have to be removed. As the biodegradable or bioerodible polymer is degraded or dissolved, the trapped azalide antibiotic is released. Although inserts can provide long term release and hence only a single application of the insert may be necessary, they are generally difficult to insert and are uncomfortable to the patient.

The preferred form is an aqueous polymeric suspension. Here, at least one of the azalide antibiotic or the polymeric suspending agent is suspended in an aqueous medium having the properties as described above. Typically the azalide antibiotic is in suspension although it is possible for the azalide antibiotic to be in solution(water soluble) or both in solution and in suspension in significant amounts generally no less than 5% in either phase (weak to moderate water solubility and relatively high total concentrations). The polymeric suspending agent is preferably a suspension (i.e. water insoluble and/or water swellable), although water soluble suspending agents are also suitable for use with a suspension of the azalide antibiotic. The suspending agent serves to provide stability to the suspension and to increase the residence time of the dosage form on the eye. It can also enhance the sustained release of the drug in terms of both longer release times and a more uniform release curve.

Examples of polymeric suspending agents include dextrans, polyethylene glycols, polyvinylpyrolidone, polysaccharide gels, Gelrite®, cellulosic polymers like hydroxypropyl methylcellulose, and carboxy-containing polymers such as polymers or copolymers of acrylic acid, as well as other polymeric demulcents. A preferred polymeric suspending agent is a water swellable, water insoluble polymer, especially a crosslinked carboxy-containing polymer.

Crosslinked carboxy-containing polymers used in practicing this invention are, in general, well known in the art. In a preferred embodiment such polymers may be prepared from at least about 90% and preferably from about 95% to about 99.9% by weight, based on the total weight of monomers present, of one or more carboxy-containing monoethylenically unsaturated monomers (also occasionally referred to herein as carboxy-vinyl polymers). Acrylic acid is the preferred carboxy-containing monoethylenically unsaturated monomer, but other unsaturated, polymerizable carboxy-containing monomers, such as methacrylic acid, ethacrylic acid, β-methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, β-phenylacrylic acid (cinnamic acid), coumaric acid (o-hydroxycinnamic acid), umbellic acid (p-hydroxycoumaric acid), and the like can be used in addition to or instead of acrylic acid.

Such polymers may be crosslinked by a polyfunctional crosslinking agent, preferably a difunctional crosslinking agent. The amount of crosslinking should be sufficient to form insoluble polymer particles, but not so great as to unduly interfere with sustained release of the azalide antibiotic. Typically the polymers are only lightly crosslinked. Preferably the crosslinking agent is contained in an amount of from about 0.01% to about 5%, preferably from about 0.1% to about 5.0%, and more preferably from about 0.2% to about 1%, based on the total weight of monomers present. Included among such crosslinking agents are non-polyalkenyl polyether difunctional crosslinking monomers such as divinyl glycol; 2,3-dihydroxyhexa-1,5-diene; 2,5-dimethyl-1,5-hexadiene; divinylbenzene; N,N-diallylacrylamide; N,N-diallymethacrylamide and the like. Also included are polyalkenyl polyether crosslinking agents containing two or more alkenyl ether groupings per molecule, preferably alkenyl ether groupings containing terminal $H_2C=C<$groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; see, e.g., Brown U.S. Pat. No. 2,798,053, the entire contents of which are incorporated herein by reference. Diolefinic non-hydrophilic macromeric crosslinking agents having molecular weights of from about 400 to about 8,000, such as insoluble di-acrylates and polyacrylates and methacrylates of diols and polyols, diisocyanate-hydroxyalkyl acrylate or methacrylate reaction products of isocyanate terminated prepolymers derived from polyester diols, polyether diols or polysiloxane diols with hydroxyalkylmethacrylates, and the like, can also be used as the crosslinking agents; see, e.g., Mueller et al. U.S. Pat. Nos. 4,192,827 and 4,136,250, the entire contents of each Patent being incorporated herein by reference.

The crosslinked carboxy-vinyl polymers may be made from a carboxy-vinyl monomer or monomers as the sole monoethylenically unsaturated monomer present, together with a crosslinking agent or agents. Preferably the polymers are ones in which up to about 40%, and preferably from about 0% to about 20% by weight, of the carboxy-containing monoethylenically unsaturated monomer or monomers has been replaced by one or more non-carboxyl-containing monoethylenically unsaturated monomer or monomers containing only physiologically and ophthalmically innocuous substituents, including acrylic and methacrylic acid esters such as methyl methacrylate, ethyl acrylate, butyl acrylate, 2-ethylhexylacrylate, octyl methacrylate, 2-hydroxyethyl-methacrylate, 3-hydroxypropylacrylate, and the like, vinyl acetate, N-vinylpyrrolidone, and the like; see Mueller et al. U.S. Pat. No. 4,548,990, the entire contents of which are incorporated herein by reference, for a more extensive listing of such additional monoethylenically unsaturated monomers.

Particularly preferred polymers are lightly crosslinked acrylic acid polymers wherein the crosslinking monomer is 2,3-dihydroxyhexa-1,5-diene or 2,3-dimethylhexa-1,5-diene. Preferred commercially available polymers include polycarbophil (Noveon AA-1) and Carbopol®. Most preferably, a carboxy-containing polymer system known by the tradename DuraSite®, containing polycarbophil, which is a sustained release topical ophthalmic delivery system that releases the drug at a controlled rate, is used in the aqueous polymeric suspension composition of the present invention.

The crosslinked carboxy-vinyl polymers used in practicing this invention are preferably prepared by suspension or emulsion polymerizing the monomers, using conventional free radical polymerization catalysts, to a dry particle size of not more than about 50 μm in equivalent spherical diameter; e.g., to provide dry polymer particles ranging in size from about 1 to about 30 μm, and preferably from about 3 to about 20 μm, in equivalent spherical diameter. Using polymer particles that were obtained by mechanically milling larger polymer particles to this size is preferably avoided. In general, such polymers will have a molecular weight which has been variously reported as being from about 250,000 to about 4,000,000, and from 3,000,000,000 to 4,000,000,000.

In the most preferred embodiment of the invention, the particles of crosslinked carboxy-vinyl polymer are monodisperse, meaning that they have a particle size distribution such that at least 80% of the particles fall within a 10 μm band of major particle size distribution. More preferably, at least 90% and most preferably at least 95%, of the particles fall within a 10 μm band of major particle size distribution. Also, a monodisperse particle size means that there is no more than 20%, preferably no more than 10%, and most preferably no more than 5% particles of a size below 1 μm. The use of a monodispersion of particles will give maximum viscosity and an increased eye residence time of the ophthalmic medicament delivery system for a given particle size. Monodisperse particles having a particle size of 30 μm and below are most preferred. Good particle packing is aided by a narrow particle size distribution.

The aqueous polymeric suspension normally contains 0.05 to 1%, preferably 0.1 to 0.5%, more preferably 0.1 to 0.5%, of the azalide antibiotic and 0.1 to 10%, preferably 0.5 to 6.5% of a polymeric suspending agent. In the case of the above described water insoluble, water-swellable crosslinked carboxy-vinyl polymer, a more preferred amount of the polymeric suspending agent is an amount ranging from 0.5 to 2.0%, preferably from 0.5% to about 1.2%, and in certain embodiments from 0.6 to 0.9%, based on the weight of the composition. Although referred to in the singular, it should be understood that one or more species of polymeric suspending agent such as the crosslinked carboxy-containing polymer can be used with the total amount falling within the stated ranges. In one preferred embodiment, the composition contains 0.6 to 0.8% of a polycarbophil such as NOVEON AA-1.

In one embodiment, the amount of insoluble lightly crosslinked carboxy-vinyl polymer particles, the pH, and the osmotic pressure can be correlated with each other and with the degree of crosslinking to give a composition having a viscosity in the range of from about 500 to about 100,000 centipoise, and preferably from about 1,000 to about 30,000 or about 1,000 to about 10,000 centipoise, as measured at room temperature (about 25° C.) using a Brookfield Digital LVT Viscometer equipped with a number 25 spindle and a 13R small sample adapter at 12 rpm. Alternatively, when the viscosity is within the range of 500 to 3000 centipoise, it may be determined by a Brookfield Model DV-11+, choosing a number cp-52 spindle at 6 rpm.

When water soluble polymers are used as the suspending agent, such as hydroxypropyl methylcellulose, the viscosity will typically be about 10 to about 400 centipoise, more typically about 10 to about 200 centipoises or about 10 to about 25 centipoise.

Aqueous polymeric suspensions of the present invention may be formulated so that they retain the same or substantially the same viscosity in the eye that they had prior to administration to the eye. Alternatively, they may be formulated so that there is increased gelation upon contact with tear fluid. For instance, when a formulation containing DuraSite® or other similar polyacrylic acid-type polymer is administered to the eye at a pH of less than about 6.7, the polymer will swell upon contact with tear fluid since it has a higher pH (around 7). This gelation or increase in gelation leads to entrapment of the suspended azalide antibiotic particles, thereby extending the residence time of the composition in the eye. The azalide antibiotic is released slowly as the suspended particles dissolve over time. All these events eventually lead to increased patient comfort and increased azalide antibiotic contact time with the eye tissues, thereby increasing the extent of drug absorption and duration of action of the formulation in the eye.

The viscous gels that result from fluid eye drops typically have residence times in the eye ranging from about 2 to about 12 hours, e.g., from about 3 to about 6 hours. The agents contained in these drug delivery systems will be released from the gels at rates that depend on such factors as the drug itself and its physical form, the extent of drug loading and the pH of the system, as well as on any drug delivery adjuvants, such as ion exchange resins compatible with the ocular surface, which may also be present.

The compositions used to topically deliver the azalide antibiotic of the present invention can be prepared from known or readily available materials through the application of known techniques by workers of ordinary skill in the art without undue experimentation. The azalide antibiotics used in the present invention are commercially available or readily obtained by a worker skilled in the art through known reactions techniques. In particular, the azalide antibiotics can be formed from erythromycin A, a naturally occurring compound formed during the culturing of a strain of *Streptomyces erythreus*. However, it is not required that the azalide antibiotic actually be formed from erythromycin. The azalide antibiotic can be combined with the other ingredients in the chosen dosage form by conventional methods known in the art.

The azalide antibiotic-containing composition is topically applied to an eye of a human or non-human animal, the latter including cows, sheep, horses, pigs, goats, rabbits, dogs, cats, and other mammals. The composition can be applied as a liquid drop, ointment, a viscous solution or gel, a ribbon or as a solid. The composition can be topically applied, without limitation, to the front of the eye, under the upper eyelid, on the lower eyelid and in the cul-de-sac. The application can be as a treatment of an infection in the eye or as a preventive such as prior to surgery.

All of the percentages recited herein refer to weight percent, unless otherwise indicated. The following non-limiting examples serve to illustrate certain features of the present invention. The compositions and amounts used for Examples 1–7 are summarized in Table 1 and for Examples 9–14 in Table 2.

Examples 1–2

Hydroxypropylmethyl cellulose, sodium chloride, edetate sodium (EDTA), BAK and surfactant are dissolved in a beaker containing approximately ⅓ of the final weight of water and stirred for 10 minutes with an overhead stirred. The azithromycin is added and stirred to disperse for 30 minutes. The solution is sterilized by autoclaving at 121° C. for 20 minutes. Alternately, the azithromycin may be dry heat sterilized and added by aseptic powder addition after sterilization. Mannitol, Poloxamer 407, and boric acid are dissolved separately in approximately ½ of the final weight of water and added by sterile filtration (0.22 μm filter) and stirred for 10 minutes to form a mixture. The mixture is adjusted to desired pH with 10N sodium hydroxide while stirring, brought to a final weight with water by sterile filtration and aseptically filled into multi-dose containers.

Examples 3–6

Noveon AA-1 is slowly dispersed into a beaker containing approximately ⅓ of the final weight of water and stirred for 1.5 hrs. with an overhead stirrer. Noveon AA-1 is an acrylic acid polymer available from B.F. Goodrich. Edetate sodium (EDTA), BAK, sodium chloride, and surfactant are then added to the polymer solution and stirred for 10 minutes after each addition. The polymer suspension is at a pH of about 3.0–3.5. The azithromycin is added and stirred to disperse for 30 minutes. The mixture is sterilized by autoclaving at 121° C., for 20 minutes. Alternately, the azithromycin may be dry heat sterilized and added by aseptic powder addition after sterilization. Mannitol, and boric acid, or sodium perborate, Dequest, mannitol, and boric acid are dissolved separately in approximately ½ of the final weight of water, added to the polymer mixture by sterile filtration (0.22 μm filter) and stirred for 10 minutes. The mixture is adjusted to the desired pH with 10N sodium hydroxide while stirring, brought to final weight with water by sterile filtration and aseptically filled into multi-dose containers.

Example 7

Noveon AA-1 is slowly dispersed into a beaked containing approximately ½ of the final weight of water and stirred for 1.5 hrs. With overhead stirrer. Noveon AA-1 is an acrylic acid polymer available from B.F. Goodrich. Edetate sodium (EDTA), Poloxamer 407, and sodium chloride are then added to the polymer suspension and stirred for 10 minutes. The polymer suspension is at a pH of about 3.0–3.5. The azithromycin is added and stirred to disperse for 30 minutes. The mixture is sterilized by autoclaving at 121° C. for 20 minutes. Alternately, the azithromycin may be dry heat sterilized and added by aseptic powder addition after sterilization. Mannitol is dissolved in 1/10 of the final weight of water and sterile filtered (0.22 μm filter) in to the polymer suspension and stirred for 10 minutes. The mixture is adjusted to desired pH with 10N sodium hydroxide while stirring, brought to final weight with water by sterile filtration and aseptically filled into unit-dose containers.

TABLE 1

Formulation Examples 1–7

| Ingredient | 1 % | 2 % | 3 % | 4 % |
|---|---|---|---|---|
| Azithromycin | 0.10 | 0.50 | 0.10 | 0.50 |
| Hydroxypropyl Cellulose | 1.50 | 2.00 | — | — |
| Noveon AA-1 | — | — | 0.80 | 0.80 |
| Sodium Chloride | 0.20 | 0.20 | 0.20 | 0.20 |
| Mannitol | 1.50 | 1.50 | 1.50 | 1.50 |
| Edetate Disodium | 0.10 | 0.10 | 0.10 | 0.10 |
| Poloxamer 407 | 0.10 | 0.10 | 0.10 | 0.10 |
| Benzalkonium Chloride | 0.01 | 0.01 | 0.01 | 0.01 |
| Sodium Perborate | — | — | — | — |
| Dequest 2060S | — | — | — | — |
| Boric Acid | 0.50 | 0.50 | 0.50 | 0.50 |
| Sodium Hydroxide | q.s. to pH 7 | q.s. to pH 7 | q.s. to pH 6 | q.s. to pH 6 |
| Water | q.s. to 100 | q.s. to 100 | q.s. to 100 | q.s. to 100 |

| Ingredient | 5 % | 6 % | 7 % |
|---|---|---|---|
| Azithromycin | 0.50 | 0.50 | 0.10 |
| Hydroxypropyl Cellulose | — | — | — |
| Noveon AA-1 | 0.80 | 0.80 | 0.80 |
| Sodium Chloride | 0.20 | 0.20 | 0.30 |
| Mannitol | 1.50 | 1.50 | 1.50 |
| Edetate Disodium | | 0.10 | 0.10 |
| Poloxamer 407 | 0.10 | 0.10 | 0.10 |
| Benzalkonium Chloride | — | 0.01 | — |
| Sodium Perborate | 0.10 | — | — |
| Dequest 2060S | 0.10 | — | — |
| Boric Acid | 0.50 | 0.50 | |
| Sodium Hydroxide | q.s. to pH 6 | q.s. to pH 7 | q.s. to pH 6 |
| Water | q.s. to 100 | q.s. to 100 | q.s. to 100 |

Example 8

An azithromycin ointment is prepared by dissolving 0.3 grams of azithromycin and 0.5 grams of chlorobutanol in a mixture containing 3.0 grams mineral oil/96.2 grams white petrolatum by stirring in a 100 ml beaker while heating sufficiently hot to dissolve both compounds. The mixture is sterile filtered through a 0.22 μm filter at a sufficient temperature to be filtered and filled aseptically into sterile ophthalmic ointment tubes.

Example 9–11

Hydroxypropylmethyl cellulose (HPMC), sodium chloride, edetate sodium (EDTA), and surfactant are dissolved in a beaker containing approximately 1/3 of the final weight of water and stirred for 10 minutes with an overhead stirrer. The mixture is sterilized by autoclaving at 121° C., for 20 minutes. The azithromycin and steroid as indicated in table 2 are dry heat sterilized and added to the HPMC-containing solution by aseptic powder addition. Mannitol, Poloxamer 407, BAK, and boric acid are dissolved separately in approximately ½ of the final weight of water and added by sterile filtration (0.22 μm filter) and stirred for 10 minutes to form a mixture. The mixture is adjusted to desired pH with 10N sodium hydroxide while stirring, brought to a final weight with water by sterile filtration, and aseptically filled into multi-dose containers.

Examples 12–14

Noveon AA-1 is slowly dispersed into a beaker containing approximately 1/3 of the final weight of water and stirred for 1.5 hrs. with an overhead stirrer. Noveon AA-1 is an acrylic acid polymer available from B.F. Goodrich. Edetate sodium (EDTA), sodium chloride, and surfactant are then added to the polymer solution and stirred for 10 minutes after each addition. The polymer suspension is at a pH of about 3.0–3.5. The mixture is sterilized by autoclaving at 121° C. for 20 minutes. The azithromycin and steroid as indicated in table 2 are dry heat sterilized and added to the polymer suspension by aseptic powder addition. BAK, mannitol, and boric acid are dissolved separately in approximately ½ of the final weight of water, added to the polymer mixture by sterile filtration (0.22 μm filter) and stirred for 10 minutes. The mixture is adjusted to the desired pH with 10N sodium hydroxide while stirring, brought to final weight with water and by sterile filtration and aseptically filled into multi-dose containers.

TABLE 2

Formulation Examples 9–14

| Ingredient | 9 % | 10 % | 11 % | 12 % | 13 % | 14 % |
|---|---|---|---|---|---|---|
| Azithromycin | 0.10 | 0.10 | 0.10 | 0.10 | 0.10 | 0.10 |
| Prednisolone Acetate | 0.10 | — | — | 0.10 | — | — |
| Fluorometholone | — | 0.10 | — | — | 0.10 | — |
| Dexamethasone | — | — | 0.10 | — | — | 0.10 |
| Hydroxypropyl methyl Cellulose | 1.50 | 1.50 | 1.50 | — | — | — |
| Noveon AA-1 | — | — | — | 0.80 | 0.80 | 0.80 |
| Sodium Chloride | 0.20 | 0.20 | 0.20 | 0.20 | 0.20 | 0.20 |
| Mannitol | 1.50 | 1.50 | 1.50 | 1.50 | 1.50 | 1.50 |
| Edetate Disodium | 0.10 | 0.10 | 0.10 | 0.10 | 0.10 | 0.10 |
| Poloxamer 407 | 0.10 | 0.10 | 0.10 | 0.10 | 0.10 | 0.10 |
| Benzalkonium Chloride | 0.01 | 0.01 | 0.01 | 0.01 | 0.01 | 0.01 |
| Boric Acid | 0.50 | 0.50 | 0.50 | 0.50 | 0.50 | 0.50 |
| Sodium Hydroxide | q.s. to pH 7 | q.s. to pH 7 | q.s. to pH 7 | q.s. to pH 6 | q.s. to pH 6 | q.s. to pH 6 |
| Water | q.s. to 100 | q.s. to 100 | q.s. to 100 | q.s. to 100 | q.s. to 100 | q.s. to 100 |

The about discussion of this invention is directed primarily to preferred embodiments and practices thereof. It will be readily apparent to those skilled in the art that further changes and modifications in actual implementation of the concepts described herein can easily be made or may be learned by practice of the invention, without departing from the spirit and scope of the invention as defined by the following claims.

We claim:
1. A process for treating an eye, comprising:
topically applying an azalide antibiotic to an eye in an amount effective to treat infection in a tissue of the eye, wherein said topically applying comprises supplying a depot of a composition containing said azalide antibiotic on the eye.

2. The process according to claim 1, wherein said eye is suffering from at least one condition selected from the group consisting of conjunctivitis, ophthalmia neonatorum, trachoma, corneal ulcers, keratitis, keratoconjunctivitis, endophthalmitis, infectious uveitis and combinations thereof, and said amount of said azalide antibiotic is therapeutically effective to treat said condition.

3. The process according to claim 1, wherein said azalide antibiotic is a compound of formula (I):

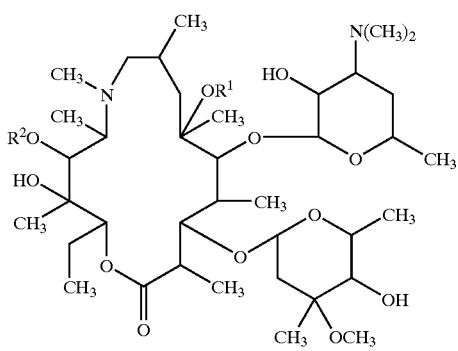

wherein $R^1$ and $R^2$ each independently represent a hydrogen atom or methyl group.

4. The process according to claim 3, wherein said azalide antibiotic is azithromycin.

5. The process according to claim 3, wherein said applying provides a therapeutically effective concentration of azalide antibiotic within a tissue of the eye for at least 8 hours.

6. The process according to claim 5, wherein said applying provides a therapeutically effective concentration of azalide antibiotic within a tissue of the eye for at least 12 hours.

7. The process according to claim 6, wherein said applying provides a therapeutically effective concentration of azalide antibiotic within a tissue of the eye for at least 18 hours.

8. The process according to claim 1, wherein said depot is an aqueous polymeric suspension of said azalide antibiotic.

9. The process according to claim 8, wherein said aqueous polymeric suspension further comprises an additional medicament.

10. The process according to claim 9, wherein said additional medicament is selected from the group consisting of amikacin, gentamycin, tobramycin, streptomycin, netilmycin, kanamycin ciprofloxacin, norfloxacin, ofloxacin, trovafloxacin, lomefloxacin, levofloxacin, enoxacin, sulfonamides, polymyxin, chloramphenicol, neomycin, paramomomycin, colistimethate, bacitracin, vancomycin, tetracyclines, rifampins, cycloserine, beta-lactams, cephalosporins, amphotericins, fluconazole, flucytosine, natamycin, miconazole, ketoconazole, corticosteroids, diclofenac, flurbiprofen, ketorolac, suprofen, comolyn, lodoxamide, levocabastin, naphazoling, antazoline, and. pheniramimane.

11. The process according to claim 1, wherein said depot is a composition selected from the group consisting of an aqueous suspensions, ointments, and inserts.

12. The process according to claim 11, wherein said composition further comprises an additional medicament.

13. The process according to claim 12, wherein said additional medicament is selected from the group consisting of antibiotics, antivirals, antifungals, anesthetics, anti-inflammatory agents, and anti-allergic agents.

14. The process according to claim 1, wherein said depot remains for at least 30 minutes after administration.

15. The process according to claim 14, wherein said depot remains for at least 4 hours after administration.

16. A topical ophthalmic composition comprising an aqueous polymeric suspension comprising water, 0.01% to 1.0% of an azalide antibiotic and 0.1 to 10% of a polymeric suspending agent, wherein said topical ophthalmic composition has an osmotic pressure of from 10 to 400 mOsM and wherein said composition does not contain constituents that are physiologically or ophthalmically harmful to the eye.

17. The composition according to claim 16, wherein said suspension further comprises an additional medicament selected from the group consisting of antibiotics, antivirals, antifungals, anesthetics, anti-inflammatory agents, and anti-allergic agents.

18. The composition according to claim 17, wherein said additional medicament is contained in the amount of from 0.01 to 5.0%.

19. The composition according to claim 17, wherein said additional medicament is selected from the group consisting of amikacin, gentamycin, tobramycin, streptomycin, netilmycin, kanamycin, ciprofloxacin, norfloxacin, ofloxacin, trovafloxacin, lomefloxacin, levofloxacin, enoxacin, sulfonamides, polymyxin, chloramphenicol, neomycin, paramomomycin, colistimethate, bacitran, vancomycin, tetracyclines, rifampins, cycloserine, beta-lactams, cephalosporins, amphotericins, fluconazole, flucytosine, matamycin, miconazole, ketoconazole, corticosteroids, diclofenac, flurbiprofen, ketorolac, suprofen, comolyn, lodoxamide, levocabastin, naphazoling, antazoline, and pheniramimane.

20. A topical ophthalmic composition comprising about 0.01 to about 5% of an azalide antibiotic, an ophthalmically acceptable carrier, and an additional medicament selected from the group consisting of antibiotics, antivirals, antifungals, anesthetics, anti-inflammatory agents, and anti-allergic agents, wherein said topical ophthalmic composition has an osmotic pressure of from 10 to 400 mOsM and wherein said composition does not contain constituents that are physiologically or ophthalmically harmful to the eye.

21. The composition according to claim 20, wherein said composition is fluid; said azalide antibiotic is contained in an amount of from about 0.01 to 2.0%; and said additional medicament is contained in an amount of from about 0.01 to 5.0%.

22. The composition according to claim 21, wherein said ophthalmically acceptable carrier is water or an aqueous solution and said additional medicament is selected from the group consisting of amikacin, gentamycin, tobramycin, streptomycin, netilmycin, kanamycin ciprofloxacin, norfloxacin, ofloxacin, trovafloxacin, lomefloxacin, levofloxacin, enoxacin, sulfonamides, polymyxin, chloramphenicol, neomycin, paramomomycin, colistimethate, bacitracin, vancomycin, tetracyclines, rifampins, cycloserine, beta-lactams, cephalosporins, amphotericins, fluconazole, flucytosine, natamycin, miconazole, ketoconazole, corticosteroids, diclofenac, flurbiprofen, ketorolac, suprofen, comolyn, lodoxamide, levocabastin, naphazoling, antazoline, and pheniramimane.

23. A process for treating an eye, comprising:
topically applying an azalide antibiotic to an eye of a non-human animal in an amount effective to treat infection in a tissue of the eye, wherein said topically applying comprises supplying a depot of a composition containing said azalide antibiotic on the eye.

24. The process according to claim 23, wherein said non-human animal is a mammal.

25. The process according to claim 23, wherein said mammal is selected from the group consisting of cows, sheep, horses, pigs, goats, rabbits, dogs, and cats.

26. The process according to claim 23, wherein said depot is an aqueous polymeric suspension of said azalide antibiotic.

27. The process according to claim 26, wherein said aqueous polymeric suspension further comprises an additional medicament.

28. The process according to claim 27, wherein said additional medicament is selected from the group consisting of amikacin, gentamycin, tobramycin, streptomycin, netilmycin, kanamycin ciprofloxacin, norfloxacin, ofloxacin, trovafloxacin, lomefloxacin, levofloxacin, enoxacin, sulfonamides, polymyxin, chloramphenicol, neomycin, paramomomycin, colistimethate, bacitracin, vancomycin, tetracyclines, rifampins, cycloserine, beta-lactams, cephalosporins, amphotericins, fluconazole, flucytosine, natamycin, miconazole, ketoconazole, corticosteroids, diclofenac, flurbiprofen, ketorolac, suprofen, comolyn, lodoxamide, levocabastin, naphazoling, antazoline, and pheniramimane.

29. The process according to claim 23, wherein said depot is a composition selected from the group consisting of an aqueous suspensions, ointments, and inserts.

30. The process according to claim 29, wherein said depot remains for at least 30 minutes after administration.

31. The process according to claim 30, therein said depot remains for at least 4 hours after administration.

32. The process according to claim 23, wherein said composition further comprises an additional medicament.

33. The process according to claim 32, wherein said additional medicament is selected from the group consisting of antibiotics, antivirals, antifungals, anesthetics, anti-inflammatory agents, and anti-allergic agents.

34. The process according to claim 23, wherein said eye is suffering from at least one condition selected from the group consisting of conjunctivitis, ophthalmic neonatorum, trachoma, corneal ulcers, keratitis, keratoconjunctivitis, endophthalmitis, infectious uveitis and combinations thereof, and said amount of said azalide antibiotic is therapeutically effective to treat said condition.

35. The process according to claim 23, wherein said azalide antibiotic is a compound of formula (I):

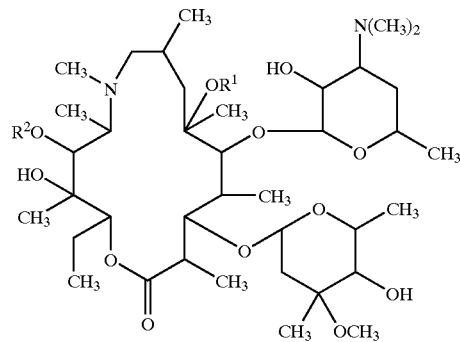

wherein $R^1$ and $R^2$ each independently represent a hydrogen atom or methyl group.

36. The process according to claim 35, wherein said azalide antibiotic is azithromycin.

37. The process according to claim 23, wherein said applying provides a therapeutically effective concentration of azalide antibiotic within a tissue of the eye for at least 8 hours.

38. The process according to claim 37, wherein said applying provides a therapeutically effective concentration of azalide antibiotic within a tissue of the eye for at least 12 hours.

39. The process according to claim 38, wherein said applying provides a therapeutically effective concentration of azalide antibiotic within a tissue of the eye for at least 18 hours.

40. The process according to claim 1, wherein the amount of said azalide antibiotic is at least about 5.0%.

41. The process according to claim 1, wherein the amount of said azalide antibiotic is from about 0.1 to about 5.0%.

42. The composition according to claim 20, wherein said composition is fluid; said azalide antibiotic is contained in an amount from at least about 5.0%, and said additional medicament is contained in an amount of from about 0.01 to 5.0%.

43. The composition according to claim 20, wherein said composition is fluid; said azalide antibiotic is contained in an amount from about 0.1 to about 5.0%, and said additional medicament is contained in an amount of from about 0.001 to 5.0%.

44. A topical ophthalmic composition comprising an aqueous polymeric suspension comprising water, from about 0.1 to about 5.0% of an azalide antibiotic, and 0.1 to 10% of a polymeric suspending agent, wherein said topical ophthalmic composition has an osmotic pressure of from 10 to 400 mOsM and wherein said composition does not contain constituents that are physiologically or ophthalmically harmful to the eye and said topical ophthalmic composition is in the form of a depot which is capable of sustained release of said azalide antibiotic.

45. The composition according to claim 20, wherein said azalide antibiotic is azithromycin.

\* \* \* \* \*